United States Patent
Mahajan et al.

(10) Patent No.: US 8,965,507 B2
(45) Date of Patent: Feb. 24, 2015

(54) SYSTEM AND METHOD FOR SELECTION OF PACING VECTORS

(71) Applicant: Cardiac Pacemakers, Inc., St. Paul, MN (US)

(72) Inventors: Deepa Mahajan, Circle Pines, MN (US); Yanting Dong, Lexington, KY (US); Sunipa Saha, Shoreview, MN (US); Holly Rockweiler, Minneapolis, MN (US); Kenneth N. Hayes, Blaine, MN (US); Krzysztof Z. Siejko, Maple Grove, MN (US); Clayton S. Foster, Andover, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 52 days.

(21) Appl. No.: 13/925,427

(22) Filed: Jun. 24, 2013

(65) Prior Publication Data
US 2014/0005742 A1    Jan. 2, 2014

Related U.S. Application Data

(60) Provisional application No. 61/667,140, filed on Jul. 2, 2012.

(51) Int. Cl.
| | | |
|---|---|---|
| *A61N 1/08* | (2006.01) | |
| *A61N 1/37* | (2006.01) | |
| *A61N 1/368* | (2006.01) | |
| *A61B 5/04* | (2006.01) | |
| *A61B 5/00* | (2006.01) | |
| *A61B 5/0452* | (2006.01) | |

(52) U.S. Cl.
CPC .............. *A61N 1/371* (2013.01); *A61N 1/3684* (2013.01); *A61N 1/3686* (2013.01); *A61B 5/04001* (2013.01); *A61B 5/0031* (2013.01); *A61B 5/0452* (2013.01)
USPC .............................................. 607/28; 607/27

(58) Field of Classification Search
USPC ..................................................... 607/27, 28
See application file for complete search history.

(56) References Cited

U.S. PATENT DOCUMENTS

| | | | |
|---|---|---|---|
| 6,650,940 | B1 | 11/2003 | Zhu et al. |
| 7,299,093 | B2 | 11/2007 | Zhu et al. |
| 7,392,086 | B2 | 6/2008 | Sathaye |
| 2002/0078968 | A1 | 6/2002 | Spinelli et al. |
| 2003/0083709 | A1 | 5/2003 | Zhu et al. |
| 2008/0294215 | A1 | 11/2008 | Sathaye |
| 2009/0210024 | A1 | 8/2009 | M. |
| 2010/0305637 | A1 | 12/2010 | McCabe et al. |
| 2010/0305638 | A1 | 12/2010 | McCabe et al. |
| 2010/0305647 | A1 | 12/2010 | McCabe et al. |
| 2011/0004264 | A1 | 1/2011 | Siejko et al. |
| 2011/0098774 | A1 | 4/2011 | Brisben et al. |

*Primary Examiner* — Joseph Dietrich
(74) *Attorney, Agent, or Firm* — Schwegman Lundberg & Woessner, P.A.

(57) ABSTRACT

Various techniques are disclosed for quickly and efficiently determining cardiac pacing vectors that minimize phrenic nerve stimulation.

20 Claims, 7 Drawing Sheets

SYSTEM AND METHOD FOR SELECTION OF PACING VECTORS

CLAIM OF PRIORITY

This application claims the benefit of priority under 35 U.S.C. §119(e) of U.S. Provisional Patent Application Ser. No. 61/667,140, entitled "SYSTEM AND METHOD FOR SELECTION OF PACING VECTORS", filed on Jul. 2, 2012, which is herein incorporated by reference in its entirety.

TECHNICAL FIELD

This disclosure relates generally to implantable medical devices, and more particularly, to implantable medical devices that deliver cardiac pacing therapy.

BACKGROUND

Cardiac rhythm management (CRM) devices can help assist heart function, such as by providing pacing electrostimulations to evoke responsive heart contractions, cardiac resynchronization therapy (CRT) electrostimulations to coordinate the spatial nature of a heart contraction of one or more heart chambers, antitachyarrhythmia pacing, cardioversion, or defibrillation shocks to interrupt a tachyarrhythmia. In order to "capture" heart tissue near an electrode delivering electrostimulation energy, evoking a responsive depolarization and heart contraction, the electrostimulation energy must exceed a threshold value, sometimes referred to as a capture threshold. After determining the capture threshold, electrostimulations can be delivered in excess of the capture threshold to capture the heart tissue—too much electrostimulation energy may not be the best for the heart, moreover, it can waste energy and shorten the useful life of the device.

OVERVIEW

The present inventors have recognized, among other things, that existing techniques of determining acceptable pacing vectors are too time consuming, where a pacing vector is at least partially defined by one or more cathodes in combination with one or more anodes. In an example, the present subject matter can provide a solution to this problem, such as by utilizing techniques that quickly and efficiently shortlist possible pacing vectors and minimize phrenic nerve stimulation during threshold testing.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

At the time of implant of a medical device configured to deliver pacing electrostimulations, a clinician, e.g., physician, can perform various measurements to assess the performance of the leads of the device, e.g., lead impedance measurements, P and R wave amplitude measurements, and pacing threshold measurements, and the like. A clinician programmer or pacing system analyzer (PSA) can be configured to perform these measurements.

Existing pacing leads, e.g., quadripolar leads having four pacing electrodes, can have over ten possible vectors available for pacing, where the one or more cathode electrodes and the one or more anode electrodes that deliver the pacing energy at least partially define the pacing vector used for pacing. Performing a search for optimal pacing vector among all available vectors can be time consuming. As such, a need exists to expedite the optimal pacing vector search, whether the patient is in an operating room as the leads are implanted, in a clinical setting for follow-up programming, or in an ambulatory setting as the device programs itself.

The present inventors have recognized, among other things, techniques for performing expedited pacing vector and automatic threshold searches, e.g., myocardial pacing thresholds and/or phrenic nerve stimulation thresholds. In some examples, the techniques can be effective in reducing the time spent searching for these thresholds. In addition, in a clinical setting, the techniques can be effective in performing a thorough threshold search and reducing the amount of time that a clinician spends searching. The techniques described below can quickly and efficiently shortlist possible pacing vectors and minimize phrenic nerve stimulation during threshold testing. In addition, at higher voltages in unipolar configurations, some patients feel discomfort or phrenic nerve/pocket stimulation. A unipolar configuration generally refers to the use of a housing electrode to sink current, i.e., anode, and one or more electrodes on one or more leads to source current, i.e., cathode(s). The techniques described in this disclosure, however, can avoid stimulating patients at higher voltages for unipolar configurations.

Figure 1:
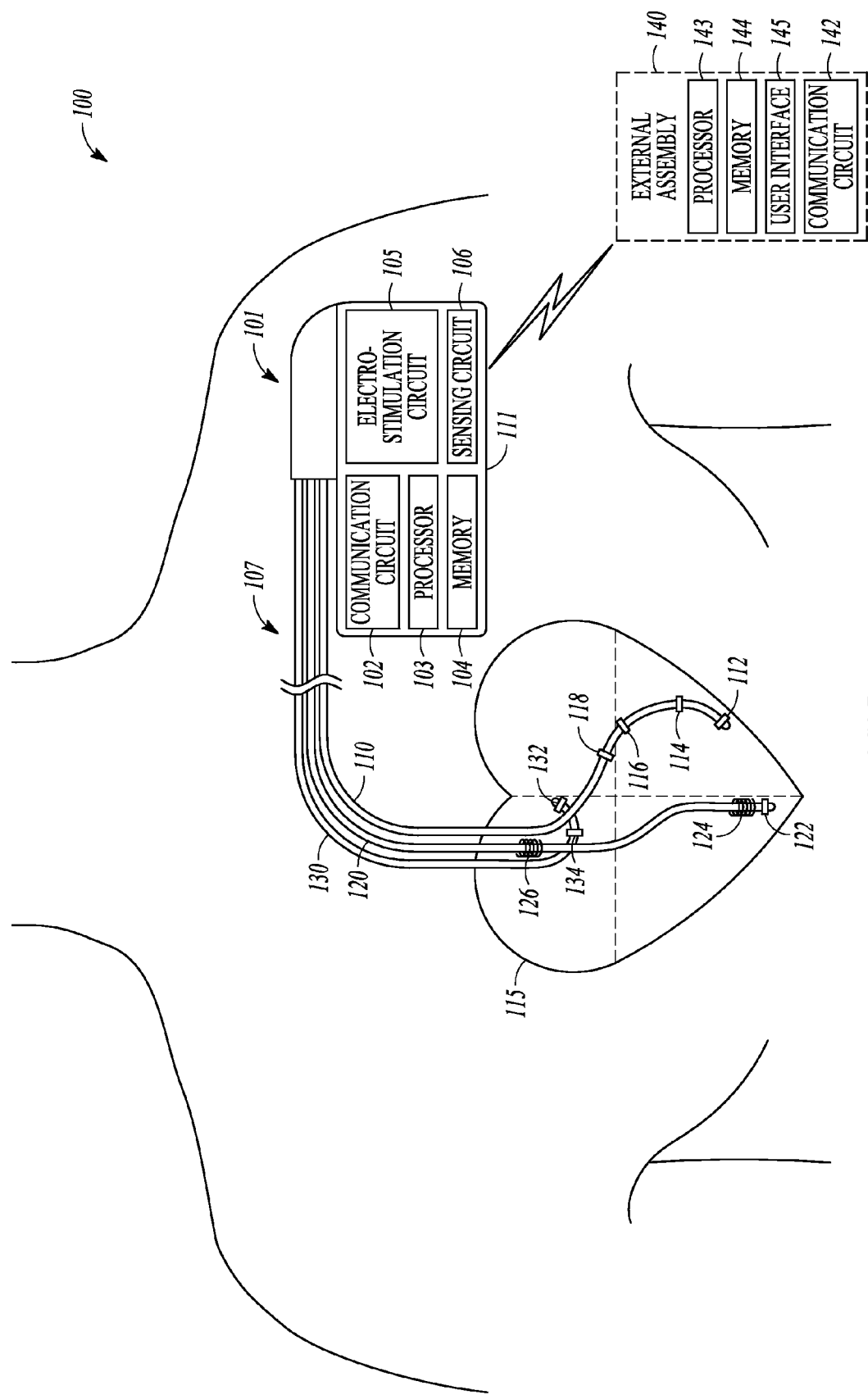
FIG. 1 illustrates an example of a portion of a system that can include an implantable or ambulatory medical device, one or more implantable leads, and an external assembly.

FIG. 1 illustrates generally an example of a system 100 that can include an implantable or ambulatory medical device 101. The ambulatory medical device 101 can be coupled to one or more electrodes, which can be carried by one or more implantable leads, such as implantable leads 110, 120, and 130. The implantable leads 110, 120, and 130 can be configured to receive or sense electrical signals from the heart 115. The ambulatory medical device 101 can include a hermetically-sealed or similar housing 111. The housing 111 can include titanium or another biocompatible material, such as one or more other conductive materials.

In an example, the ambulatory medical device 101 can include one or more of a pacemaker, a defibrillator, an implantable monitor, a drug delivery device, a cardiac resynchronization therapy (CRT) device, a neural stimulation device, or one or more other implantable assemblies configured to monitor a person or configured to provide one or more treatments to the person. Examples of such monitoring or treatment can include electrostimulation of tissue such as cardiac tissue, or electrical monitoring of muscular or cardiac activity. In an example, the ambulatory medical device 101 can include an external medical device, such as a pacing system analyzer, or other external medical device that can be used to configure a system of multipolar implantable leads.

In the example of FIG. 1, the ambulatory medical device 101 can be coupled to a heart 115, or other body tissue, such as via the electrode system 107, epicardial electrodes, or external (e.g., skin-patch) electrodes. The electrode system 107 can include at least one lead and at least one electrode for each lead. FIG. 1 shows an example in which there are three implantable leads 110, 120, and 130. In the example of FIG. 1, the implantable lead 110 can be configured for use in association with a left ventricle of the heart 115. For example, the implantable lead 110 can be sized and shaped to allow insertion into a coronary sinus and intravascular advancement such as to put at least one electrode in association with the left ventricle of the heart. The implantable lead 110 can be a multipolar lead, including a plurality of electrodes and corresponding conductors. In an example, the implantable lead 110 can include four discrete electrodes, such as: a tip electrode 112, a first ring electrode 114, a second ring electrode 116, and a third ring electrode 118. In an example, the electrodes 114, 116, and 118 can be located near a distal portion of the implantable lead 110. Each of the electrodes 114, 116, and 118 can be separated by electrically insulating material, thus electrically isolating the individual electrodes. Each of the four left ventricular electrodes 112, 114, 116, and 118 can correspond to a unique electrical conductor and can be individually addressable by a sensing circuit 106 or an electrostimulation circuit 105 contained within the ambulatory medical device 101.

In the example of FIG. 1, the implantable lead 120 can include a tip electrode 122, a first coil electrode 124, and a second coil electrode 126. As generally shown in FIG. 1, the implantable lead 120 can, in an example, be inserted into the right atrium and right ventricle of the heart 115 so that the first coil electrode 124 is positioned in the right ventricle and the second coil electrode 126 is positioned in the right atrium.

In the example of FIG. 1, the implantable lead 130 can include a tip electrode 132 and a ring electrode 134. As generally shown in FIG. 1, the implantable lead 130 can be configured for insertion into the right atrium of the heart 115. The physical illustration of the implantable leads 110, 120, and 130 provided in FIG. 1 are provided for illustration purposes only and are non-limiting examples of leads that can be used to perform various functions attributed to the device 101.

The external assembly 140 can be an adjunct (e.g., non-ambulatory) external assembly. In an example, the external assembly 140 can include the ambulatory medical device 101 features described above and below, such that the external assembly 140 can be configured to be coupled to the electrode system 107. The ambulatory medical device 101 can be configured to communicate (wired or wirelessly) with a local or remote external device, such as external assembly 140. This can include using an RF, optical, acoustic, or other communication link. The external assembly 140 can be a portion or part of a patient management system. In an example, the external assembly 140 can communicate with one or more remote clients, such as web-based clients, or can be communicatively coupled to one or more servers, which can include medical and patient databases.

In an example, the ambulatory medical device 101 can include a communication circuit 102, a processor circuit 103, a memory circuit 104, an electrostimulation circuit 105, or a sensing circuit 106. The processor circuit 103 and memory circuit 104 can be used to control the operation of the ambulatory medical device 101. For example, the processor circuit 103 can be programmed to detect a cardiac condition, such as by using the sensing circuit 106 or another physiological sensor, and to respond to the detected cardiac condition, such as by using the electrostimulation circuit 105. The memory circuit 104 can include one or more parameters, such as for various pacing and sensing modes, test procedures or the like. The memory circuit 104 can be configured to store physiological data, such as data concerning the condition of the heart 115. The memory circuit 104 can be configured to store device data, such as data about a status of a test or a test result. In an example, the ambulatory medical device 101 can use the electrostimulation circuit 105 or the sensing circuit 106 to interface with the electrode system 107. The electrostimulation circuit 105 or the sensing circuit 106 can be configured to generate an electrostimulation signal, the electrostimulation circuit 105 or the sensing circuit 106 can be electrically coupled to the electrode system 107, and the electrostimulation signal can be transmitted from the electrostimulation circuit 105 or the sensing circuit 106 to the heart 115 via the electrode system 107. The communication circuit 102 can be configured to establish a data communication link between the ambulatory medical device 101 and the external assembly 140.

The external assembly 140 can include a communication circuit 142, a processor circuit 143, a memory circuit 144, or a user interface 145. In an example, the communication circuit 142 can include inductive coils or radio frequency telemetry circuitry, and can be configured to communicate with the ambulatory medical device 101. The processor circuit 143 and memory circuit 144 can be used to interpret information received from the user interface 145, or can be used to determine when to use the communication circuit 142 to exchange information with the ambulatory medical device 101. In an example, the processor circuit 143 and memory circuit 144 can be used to initiate an electrostimulation test performed by the external assembly 140 using the electrode system 107. The external assembly 140 can be used to perform electrostimulation tests using the electrode system 107 and can be configured to display results such as by using the user interface 145.

In the example of FIG. 1, the user interface 145 can include, but is not limited to, a keyboard, a mouse, a light pen, a touch-screen, a display screen, a printer, or an audio speaker. In an example, the user interface 145 can be configured as a full color, high definition graphical display, such as using an LCD computer monitor. In an example, the user interface 145 can be configured for use as a monochromatic display, such as using a monitor to display text. In an example, the user interface 145 can be configured to interactively present a graphical representation of electrostimulation electrodes or vectors to a user. In another example, the user interface 145 can be configured to interactively present a text-based representation of electrostimulation electrodes or vectors.

Using the techniques of this disclosure, the device 101 and, in some example configurations, the external assembly 140 can perform expedited automatic threshold searches, e.g., to find myocardial pacing thresholds and/or phrenic stimulation thresholds, that can be effective in reducing the overall vector search time. As described in more detail below, these techniques can quickly and efficiently shortlist possible pacing vectors associated with the electrodes of the leads 110, 120, 130 and a housing electrode (not depicted), and can minimize phrenic nerve stimulation during threshold testing.

Figure 2:
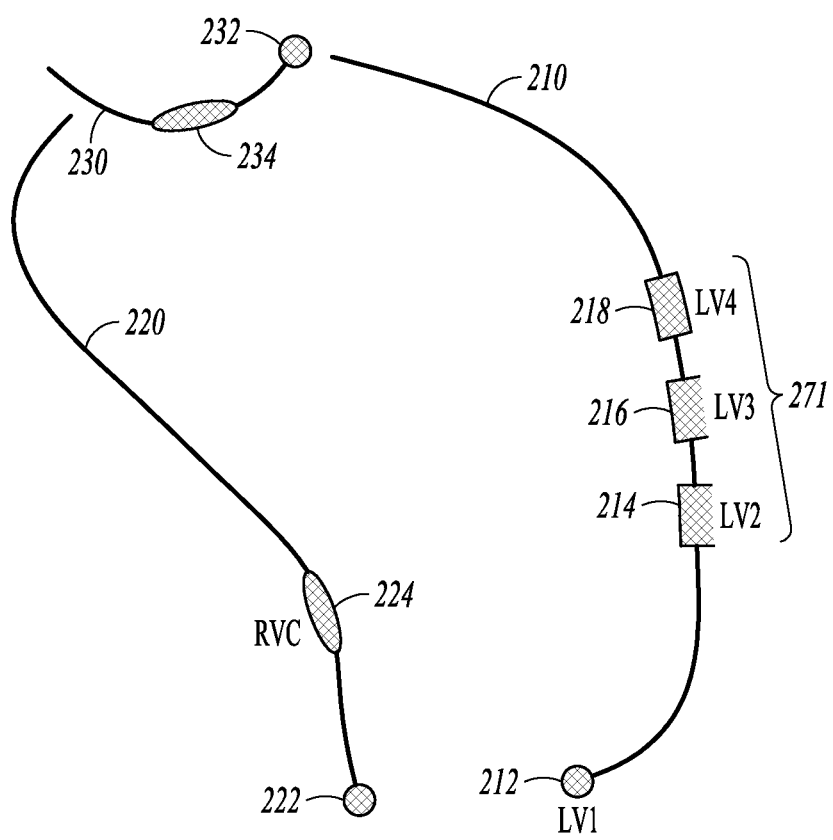
FIG. 2 is a diagram illustrating the leads depicted in FIG. 1 in more detail.

FIG. 2 is a diagram illustrating the leads depicted in FIG. 1 in more detail. A clinician may want to configure the ambulatory medical device 101, such as to effectively and efficiently pace a heart using the set of multipolar leads. However, the multipolar leads can include several electrostimulation electrodes per lead and, therefore, the set of pacing and sensing configurations available to the clinician can be numerous. It can be a lengthy and cumbersome task for the clinician to define and test each potential pacing or sensing configuration, such as for efficacy and efficiency. As described in more detail below with respect to FIGS. 4-6, this disclosure describes techniques for performing expedited automatic threshold searches, e.g., to find myocardial pacing thresholds and/or phrenic stimulation thresholds, that can be effective in reducing the time spent searching for these thresholds.

FIG. 2 depicts three multipolar implantable leads of the device 101 of FIG. 1. More particularly, FIG. 2 depicts a multipolar left ventricular lead 210, a right ventricular lead 220, and an atrial lead 230. Left ventricular lead 210 comprises a left ventricular tip electrode 212 ("LV1") at the distal end of the lead, and three ring electrodes 214 ("LV2"), 216 ("LV3"), and 218 ("LV4"), the three ring electrodes positioned near the left ventricle of the heart. Each of the ring electrodes 214, 216, and 218 can be electrically isolated from one another and can be individually addressable by the ambulatory medical device 101, or by the external assembly 140, such as described above in the discussion of FIG. 1. Right ventricular lead 220 comprises a right ventricular tip electrode 222, and a right ventricular defibrillation coil electrode 224 ("RVC"). The housing 111 of the ambulatory medical device 101 of FIG. 1 can also include an electrode 211 (not depicted).

The cathode and anode electrodes that deliver the pacing energy at least partially define a pacing vector used for pacing. Each electrode shown in FIG. 2 can be configured as a cathode and combined with another electrode configured as an anode to form a pacing vector resulting in numerous possible vectors available for testing. Evaluating all possible vectors is time consuming and undesirable, particularly at the time of implant.

In accordance with this disclosure and as described in more detail below with respect to FIGS. 4-6, a set of at least two pacing vectors for evaluation/testing is defined that includes less than all permutations of the electrodes. In one example, the set of at least two pacing vectors is less than the total number of pacing vectors available for pacing Each vector is at least partially defined by a first electrode, e.g., cathode, and a second electrode, e.g., anode. A user, e.g., clinician, can define the initial set of vectors for evaluation/testing to include only pairings of electrodes that the user believes will be efficacious. Or, a predefined set of electrode pairings can be stored in memory as vectors, e.g., default vectors. Or, the user can enter information regarding the particular leads and electrodes implanted in the patient and the microprocessor 364, for example, can determine a set of electrode pairings based on the lead and electrode information.

Generally speaking, after the set of electrodes is defined, the device 101 delivers at least one first pacing stimulus at a first specified pacing energy, e.g., voltage amplitude, current amplitude, pulse width, and the like, and a "first pass" is performed in which each electrode in the set of at least two pacing vectors to be tested is tested first as a cathode ("cathode switching"), where each cathode to be tested is associated with a predefined electrode assigned as an anode. The predefined electrode assigned as anode can be a default anode or it can be assigned by a clinician prior to testing. One objective of the first pass is to eliminate any non-usable or unacceptable cathodes and categorize the remaining cathodes. Non-usable or unacceptable cathodes includes those cathodes that cause phrenic stimulation, create a hemodynamically unstable environment, and/or have a myocardial pacing threshold, e.g., left ventricle threshold, higher than the phrenic stimulation threshold. As described in more detail below, the categorized cathodes can also be prioritized.

After the cathodes are categorized following the first pass, a "second pass" is performed in which each electrode in the initially identified set of electrodes to be tested, except the predefined anode, is tested as an anode ("anode switching"). One objective of the second pass is to recommend one or more vectors with the lowest myocardial pacing threshold, e.g., left ventricle threshold or right ventricle threshold, and the largest phrenic stimulation margin, e.g., a difference between the phrenic stimulation threshold and one of a capture threshold and a program pacing amplitude.

Figure 3:
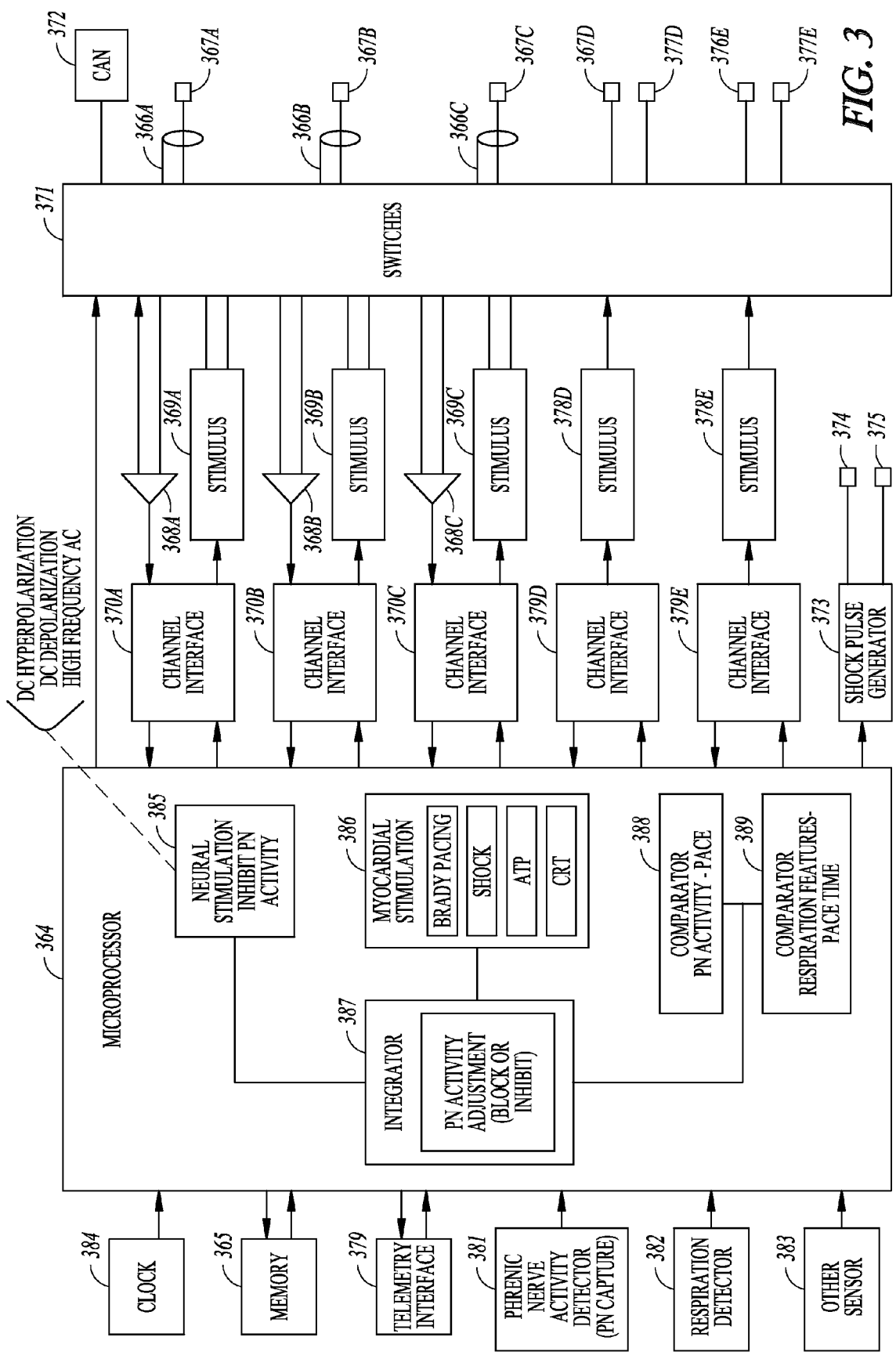
FIG. 3 illustrates a system diagram of an embodiment of a microprocessor-based implantable device.

FIG. 3 illustrates a system diagram of an embodiment of a microprocessor-based implantable device. The controller of the device is a microprocessor 364 which communicates with a memory 365 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 366A-C and tip electrodes 367A-C, sensing amplifiers 368A-C, pulse generators 369A-C, and channel interfaces 370A-C. In some embodiments, the leads of the cardiac stimulation electrodes are replaced by wireless links. Each channel thus includes a pacing channel made up of the pulse generator connected to the electrode and a sensing channel made up of the sense amplifier connected to the electrode. The channel interfaces communicate bidirectionally with the microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects intrinsic chamber activity, termed either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 371 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar or in an extended bipolar mode using only one of the electrodes of the lead with the device housing (or "can") 372 or an electrode on another lead serving as a ground electrode. A shock pulse generator 373 is also interfaced to the controller for delivering a defibrillation shock via a pair of shock electrodes 374 and 375 to the atria or ventricles upon detection of a shockable tachyarrhythmia. A can electrode may be used to deliver shocks.

Neural stimulation channels, identified as channels D and E, are incorporated into the device, where one channel includes a bipolar lead with a first electrode 376D and a second electrode 377D, a pulse generator 378D, and a channel interface 379D, and the other channel includes a bipolar lead with a first electrode 376E and a second electrode 377E, a pulse generator 378E, and a channel interface 379E. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, and the like. In this embodiment, each of the neural stimulation channels uses a lead which can be intravascularly disposed near an appropriate neural target. Other types of leads and/or electrodes may also be employed. A nerve cuff electrode may be used in place of an intravascularly disposed electrode to provide neural stimulation. In some embodiments, the leads of the neural stimulation electrodes are replaced by wireless links. The figure illustrates a telemetry interface 379 connected to the microprocessor, which can be used to communicate with an external device.

Various embodiments include one or more of the following: a pace-induced phrenic nerve activity detector 381 to detect phrenic nerve capture, a respiration detector 382 and/or other sensor(s) 383 such as to provide contextual information like activity and posture. According to various embodiments, the phrenic nerve activity detector may include, but is not limited to, an accelerometer, an acoustic sensor, a respiration sensor, impedance sensors, neural sensor on the phrenic nerve, or electrodes to sense electromyogram signals indicative of diaphragm contraction. Various embodiments use more than one detector to provide a composite signal that indicates phrenic nerve capture. The illustrated embodiment also includes a clock 384.

The illustrated microprocessor 364 is capable of performing phrenic nerve traffic inhibition routines 385, and cardiac tissue (e.g. myocardial) stimulation routines 386. Examples of phrenic nerve traffic inhibition routines include hyperpolarization of the nerve axons using a DC current pulse; depolarization of the nerve axons using a DC current pulse; and/or a high-frequency AC waveform (>1 KHz). Examples of myocardial therapy routines include bradycardia pacing therapies, anti-tachycardia shock therapies such as cardioversion or defibrillation therapies, anti-tachycardia pacing therapies (ATP), and cardiac resynchronization therapies (CRT). The illustrated controller is able to perform routines 387 to integrate myocardial stimulation with phrenic nerve traffic inhibition to avoid pace-induced phrenic nerve activity. The illustrated controller 364 also includes a comparator 388 to compare time when phrenic nerve activity is detected to a pace time to determine that the phrenic nerve activity is attributed to the pace. The controller 364 also includes a comparator 389 to compare respiration features to the pace time, and enable the phrenic nerve traffic inhibition if the pace time occurs during a programmed time of the respiration.

The neural stimulation to inhibit phrenic nerve activity and cardiac rhythm management functions may be integrated in the same device, as generally illustrated in FIG. 3 or may be separated into functions performed by separate devices. One of ordinary skill in the art will understand that, the modules and other circuitry shown and described herein can be implemented using software, hardware, firmware and combinations thereof.

Figure 4:
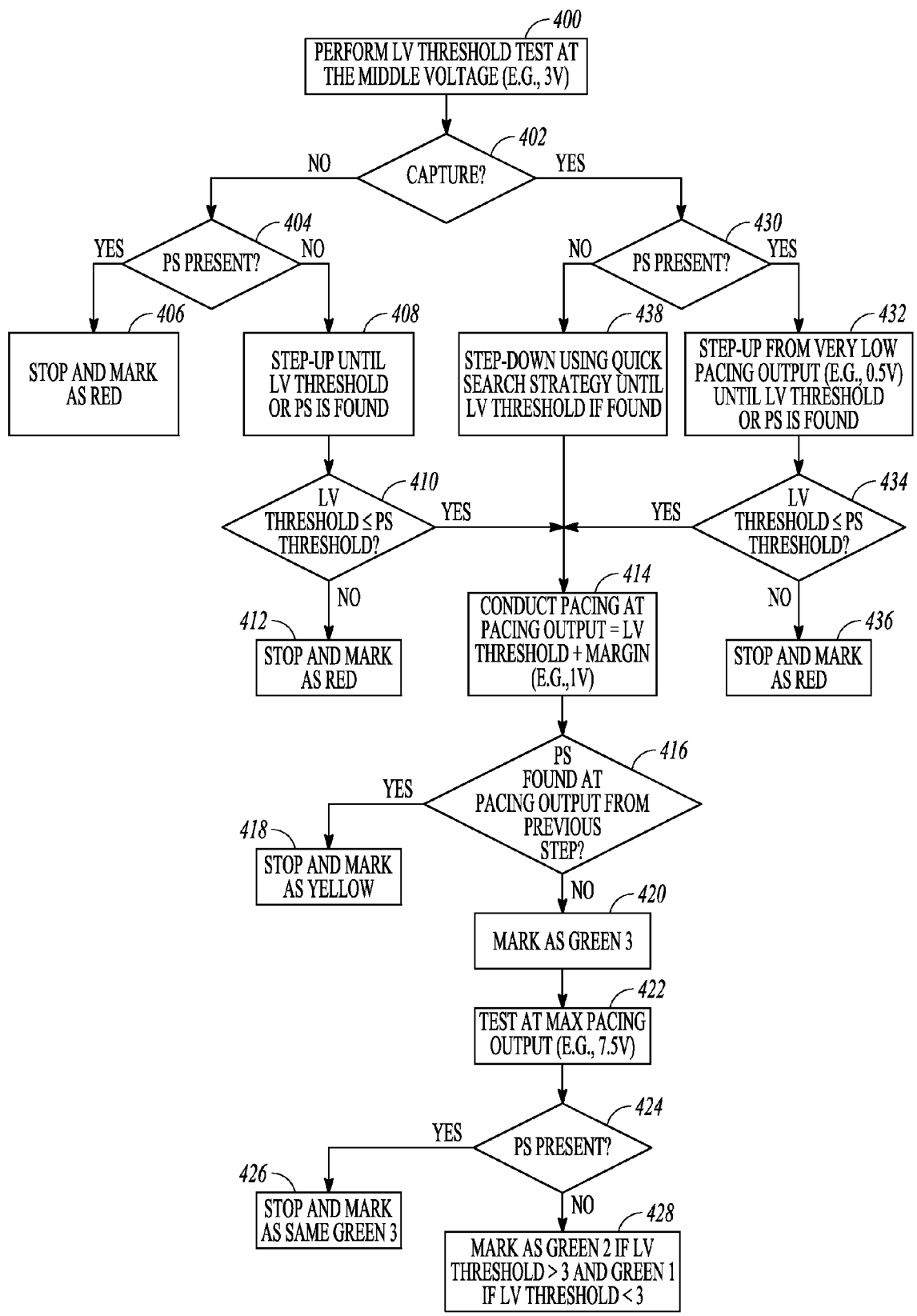
FIG. 4 is a flow diagram illustrating a portion of an example method for evaluating a plurality of vectors in accordance with this disclosure.

FIG. 4 is a flow diagram illustrating a portion of an example method for evaluating a plurality of vectors in accordance with this disclosure. In FIG. 4, a "first pass" is performed in which each electrode in a set of at least two pacing vectors to be tested is tested first as a cathode ("cathode switching"), where each cathode to be tested is associated with a predefined electrode assigned as an anode. One objective of the first pass of FIG. 4 is to eliminate any non-usable or unacceptable cathodes and categorize the remaining cathodes. Non-usable or unacceptable cathodes includes those cathodes that cause phrenic stimulation and/or have a myocardial pacing threshold, e.g., left ventricle threshold, higher than the phrenic stimulation threshold. As described in more detail below, the categorized cathodes can also be prioritized.

In some example implementations, the set of electrodes to be tested includes less than all permutations of the electrodes. For example, a user, e.g., clinician, can define the set of electrodes to include only pairings of electrodes that the user believes will be efficacious. Or, a predefined set of electrode pairings can be stored in memory, e.g., default vectors. Or, the user can enter information regarding the particular leads and electrodes implanted in the patient and the microprocessor 364, for example, can determine a set of electrode pairings based on the lead and electrode information. In one example implementation, the set of electrodes on which the threshold test techniques described in this disclosure can be run can be selected on the basis of pacing vector rankings, as described in detail in U.S. Patent Application Publication No. 2011/0004264 to Siejko et al., the entire content of which being incorporated herein by reference.

As described in more detail below with respect to FIG. 5, in a "second pass," each electrode in the set of electrodes to be tested, except the predefined anode, is tested second as an anode. In some example implementations, however, the first pass can test anodes and the second pass can test cathodes.

In FIG. 4, one of the plurality of vectors in the initial set of two or more pacing vectors to be tested is selected, pacing is turned on, and implantable medical device 101 delivers at least one first pacing stimulus at a first specified pacing energy, e.g., voltage amplitude, current amplitude, pulse width, and the like, to perform a threshold test (400), e.g., left ventricle threshold test or right ventricle threshold test. The techniques of this disclosure are also generally applicable to threshold testing of the right and left atrium.

In one example, the first specified pacing energy has a voltage amplitude near the middle of a set of pacing ranges, e.g., at about 3.0 V. For example, as part of the first pass, a user, e.g., clinician, can select the coil electrode 234 to sink current sourced by the ring electrode 214 as a cathode to sink the current at the coil electrode 234 (both of FIG. 2) as a first vector. The device 101 can deliver a pacing stimulus, e.g., pulse, via the electrodes 214, 234 to the heart 115. The pacing stimulus can be a voltage stimulus or a current stimulus. In some examples, the pacing stimulus can have a pulse width defined by a duty cycle having an ON:OFF ratio, where ON is the time during which stimulation energy is delivered and where OFF is the time between successive pulses during which no stimulation energy is delivered. Although the techniques of FIGS. 4-6 are described below with respect to voltages, similar strategies can be used with respect to current and pulse width.

Device 101 and, more particularly, microprocessor 364 of FIG. 2, can determine whether, in response to the delivered first pacing stimulus, a first cardiac depolarization occurred capture (402) by monitoring one or more physiological signals indicative of capture of the heart, e.g., a signal such as evoked response, as well as hemodynamic response, LV-RV timings, and the like. In some example implementations, microprocessor 364 can automatically determine whether the pacing stimulus captured the heart by processing one or more received signals. In other examples, microprocessor 364 can process one or more received signals and display the results to a user, e.g., clinician, to allow the user to determine whether the pacing stimulus captured the heart. Microprocessor 364 can display the results to a user via an electrogram, for example, thereby allowing the user to determine whether there was loss of capture. Capture detection is well known to those of ordinary skill in the art and, as such, all the various methods for determining whether capture occurred will not be described in detail in this disclosure.

If the pacing stimulus did not capture ("NO" branch of block 402), then a determination is made whether, in response to the delivered at least one first pacing stimulus, a first phrenic nerve stimulation occurred (404). In some examples, device 101 can determine phrenic stimulation automatically, e.g., using physiological information received in response to the delivered at least one first pacing stimulus. In other examples, a user, e.g., clinician, can manually determine whether phrenic stimulation occurred by asking the patient if he/she is experiencing diaphragmatic contraction, or by observing the patient for signs of diaphragmatic contraction, which can be indicative of phrenic stimulation.

If phrenic stimulation is present ("YES" branch of block 404), then the microprocessor 364 can categorize the first electrode based on these results and then stop testing the vector (406), where the first electrode can be the cathode that is being tested and the anode is the predefined anode that is associated with that cathode. In the particular example described above, the microprocessor 364 can categorize the cathode as undesirable because the phrenic stimulation threshold is less than the myocardial pacing capture threshold (the pacing stimulus did not capture but did produce phrenic stimulation). In one example, the microprocessor 364 can categorize such vectors in terms of a color, such as red, to indicate that the vector is undesirable and should not be used for pacing. In other examples, a numerical value can be assigned to such vectors to indicate their efficacy.

If phrenic stimulation is not present ("NO" branch of block 404), then the microprocessor 364 can adjust the pacing stimulus to determine a first pacing threshold value by iteratively increasing the amplitude or pulse width of the pacing stimulus, and then device 101 can deliver another pacing stimulus, using the same vector initially selected, at the increased amplitude until the pacing stimulus captures the heart and/or phrenic stimulation occurs (408). If the myocardial pacing capture threshold, e.g., left ventricle threshold or right ventricle threshold, is not less than the phrenic stimulation threshold ("NO" branch of block 410), then the microprocessor 364 can categorize the acceptability of the first electrode, e.g., cathode, based on these results and then stop testing the vector (412). In this manner, the acceptability of the first electrodes, e.g., cathodes, of the two or more pacing vectors are categorized using information about at least one of the determined first pacing threshold value, whether the first cardiac depolarization occurred, or whether the first phrenic nerve stimulation occurred.

In the particular example described above, the microprocessor 364 can categorize the cathode as undesirable because the phrenic stimulation threshold is less than the myocardial pacing capture threshold. As indicated above, the microprocessor 364 can categorize the acceptability of such cathodes in terms of a color, such as red, to indicate that the vector is undesirable and should not be used for pacing.

If the myocardial pacing capture threshold, e.g., left ventricle threshold or right ventricle threshold, is less than the phrenic stimulation threshold ("YES" branch of block 410), then the microprocessor 364 can control the device 101 to adjust the pacing stimulus and deliver a pacing stimulus at a pacing output equivalent to the determined amplitude plus a safety margin value, e.g., a user-specified safety margin value of 1 V (414). If phrenic stimulation is determined to have occurred at the pacing output ("YES" branch of block 416), e.g., either automatically or manually by a clinician, then the microprocessor 364 can categorize the acceptability of the tested cathode, based on these results, and then stop testing the vector (418). The acceptability of the cathode is based on the relationship between the capture threshold and the phrenic stimulation thresholds to the safety margin, where the sum of the capture threshold value and the safety margin value is less than the phrenic stimulation threshold.

In the particular example described above, the microprocessor 364 can categorize the cathodes as a possible cathode that can be used for pacing. For example, the microprocessor 364 can categorize the cathode as yellow to indicate that the cathode can be used, but may not be the most desirable cathode available for pacing because phrenic stimulation occurred at the pacing output.

If phrenic stimulation is determined to have not occurred at the pacing output ("NO" branch of block 416), then the microprocessor 364 can categorize the cathode based on these results. In the particular example described above, the microprocessor 364 can categorize the cathode as a possible cathode that can be used for pacing. For example, the microprocessor 364 can categorize the cathode as green to indicate that the cathode can be used for pacing purposes given that the cathode captured the heart and that the cathode did not cause any phrenic stimulation. Furthermore, the microprocessor 364 can, for example, tentatively assign a level of green to the cathode (420), e.g., level 3 green, to indicate that although the cathode can be used for pacing, other cathodes might be more desirable.

In one example implementation, a user, e.g., a clinician, can run the complete test to find the categorization of all possible cathodes. In another example implementation, the user can stop the test after finding one green cathode. For example, in a clinical setting, real time performance can be observed and the test can be stopped once the test finds a green cathode.

Next, the microprocessor 364 controls the device 101 to increase the amplitude of the pacing stimulus to the device's maximum pacing output, e.g., about 7.5 V (422). If phrenic stimulation is determined to have occurred at the maximum pacing output ("YES" branch of block 424), e.g., either automatically or manually by a clinician, then the microprocessor 364 can retain the previous categorization of the vector, e.g., level 3 green, based on these results and then stop testing the cathode (426). If phrenic stimulation is determined to have not occurred at the maximum pacing output ("NO" branch of block 424), e.g., either automatically or manually by a clinician, then the microprocessor 364 can re-categorize the cathode based on these results (428).

For example, if the myocardial pacing capture threshold, e.g., left ventricle threshold or right ventricle threshold, is greater than about 3 V, then the microprocessor 364 can categorize the cathode as level 2 green, for example. If, however, the myocardial pacing capture threshold, e.g., left ventricle threshold, is less than about 3 V, then the microprocessor 364 can categorize the cathode as level 1 green, for example, where a level 1 green cathode is more desirable than a level 2 green cathode, and a level 2 green cathode is more desirable than a level 3 green cathode.

In this manner, cathodes can be categorized, e.g., as a green cathode, yellow cathode, red cathode, and the like. In addition, the categorized cathodes can be prioritized or ranked. For example, as indicated above, a level 1 green cathode can have a higher priority, or be ranked higher, than a level 2 green cathode, and a level 2 green cathode can have a higher priority, or be ranked higher, than a level 3 green cathode. In addition, any green cathode, e.g., level 1, level 2, level 3, can have a higher priority, or be ranked higher, than a yellow cathode, and a yellow cathode can have a higher priority, or be ranked higher, than a red cathode.

Returning to near the top of the flow diagram in FIG. 4, if the initial delivered pacing stimulus did capture the heart ("YES" branch of block 402), then a determination is made regarding whether a phrenic nerve stimulation occurred (430). If phrenic stimulation is present ("YES" branch of block 430), then the microprocessor 364 can adjust the pacing stimulus to a much lower level (e.g., 0.5 V) and then determine a pacing threshold value by iteratively increasing the amplitude of the pacing stimulus and device 101 can deliver another pacing stimulus, using the same vector initially selected, at the increased amplitude until the pacing stimulus captures the heart and/or phrenic stimulation occurs (432).

If the myocardial pacing capture threshold, e.g., left ventricle threshold or right ventricle threshold, is not less than the phrenic stimulation threshold ("NO" branch of block 434), then the microprocessor 364 can categorize the acceptability of the first cathode based on these results and then stop testing the vector (436). That is, the microprocessor 364 can categorize the acceptability of the first electrode using information about at least one of the determined first pacing threshold value, whether the first cardiac depolarization occurred, or whether the first phrenic nerve stimulation occurred.

In the particular example described above, the microprocessor 364 can categorize the cathode as undesirable because the phrenic stimulation threshold is lower than the myocardial pacing capture threshold. As indicated above, the microprocessor 364 can categorize such cathodes in terms of a color, such as red, to indicate that the cathode is undesirable and should not be used for pacing.

If, however, the myocardial pacing capture threshold, e.g., left ventricle threshold or right ventricle threshold, is less than the phrenic stimulation threshold ("YES" branch of block 434), then the microprocessor 364 can control the device 101 to adjust the pacing stimulus and deliver a pacing stimulus at a pacing output equivalent to the determined amplitude plus a safety margin value, e.g., a user-specified safety margin value of 1 V (414). The remaining decision blocks were described above and, for purposes of conciseness, will not be described again.

If phrenic stimulation is not present ("NO" branch of block 430), then the microprocessor 364 can adjust the pacing stimulus, e.g., pacing pulse, to determine a first pacing threshold value by iteratively decreasing, or stepping down, the amplitude of the pacing stimulus, and device 101 can deliver another pacing stimulus, using the same vector initially selected, at the decreased amplitude until the pacing stimulus captures the heart (438). In one example, the microprocessor 364 can iteratively decrease, or step down, the amplitude of the pacing stimulus using step sizes that that have fixed increments. The step-down search strategy can, in some examples, be incorporated into the automatic threshold algorithm to facilitate automatic and quick threshold searching.

In other examples, the step sizes can have variable increments, e.g., as determined by the amplitude of the pacing output. By way of specific example, the following step sizes can be used: for a pacing output voltage that is less than 1 V, a 0.1 V step size can be used; for a pacing output voltage that is less than 2 V and greater than 1 V, a 0.2 V step size can be used; and for a pacing output voltage that is greater than 2 V, a 0.5 V step size can be used.

In another example implementation, a binary search strategy can be used to iteratively decrease the amplitude of the pacing stimulus until the pacing stimulus captures the heart and/or phrenic stimulation occurs. For example, the step-down amplitude of the next voltage tested can be half of the previous voltage, or $V_{i+1}=V_i/2$. If $V_{i+1}$ captures the heart, then the amplitude of the next voltage tested can be half of the previous voltage, or $V_{i+2}=V_{i+1}/2$. But, if $V_{i+1}$ does not capture the heart, then the amplitude of the next voltage tested can be the average of the previous two voltages, or $V_{i+2}=(V_i+V_{i+1})/2$. In some implementations, the resulting voltage $V_{i+2}$ can be rounded to the nearest increment.

Whether a binary search strategy or a decreasing step size search strategy is used, it can be desirable to have one or more conditions that, if met, halt the search. As one example, if a number of iterations is met or exceeded, the search may halt. As another example, if a number of changes in direction in the search is met or exceeded, the search may halt. As another example, if a difference between $V_i$ and $V_{i+1}$ is less than a predetermined value or within a predetermined range, the search may halt. Halting the search can help expedite the process of categorizing vectors.

After the microprocessor 364 adjusts the pacing stimulus by iteratively decreasing, or stepping down, the amplitude of the pacing stimulus and determines a myocardial pacing threshold voltage (438), then the microprocessor 364 can control the device 101 to deliver a pacing stimulus at a pacing output equivalent to the determined amplitude plus a safety margin value, e.g., a user-specified safety margin value of 1 V (414). The remaining decision blocks were described above and, for purposes of conciseness, will not be described again.

In this manner, a first electrode, e.g., cathode, is tested and categorized based on its acceptability using information about at least one of the determined pacing threshold values, whether the cardiac depolarization occurred, or whether the phrenic nerve stimulation occurred. The techniques described above with respect to the "first pass" of FIG. 4 are repeated for each cathode in the initially identified set of electrodes until all electrodes have been tested as cathodes and categorized using information about at least one pacing threshold values, whether the cardiac depolarization occurred, or whether first phrenic nerve stimulation occurred. Again, in some examples, the first pass of FIG. 4 can test each electrode in the initially identified set of electrodes as anodes and then as cathodes in the second pass, described below with respect to FIG. 5. In the second pass, described below with respect to FIG. 5, each electrode in the initially identified set of electrodes is tested as an anode and categorized based on its acceptability.

Figure 5:
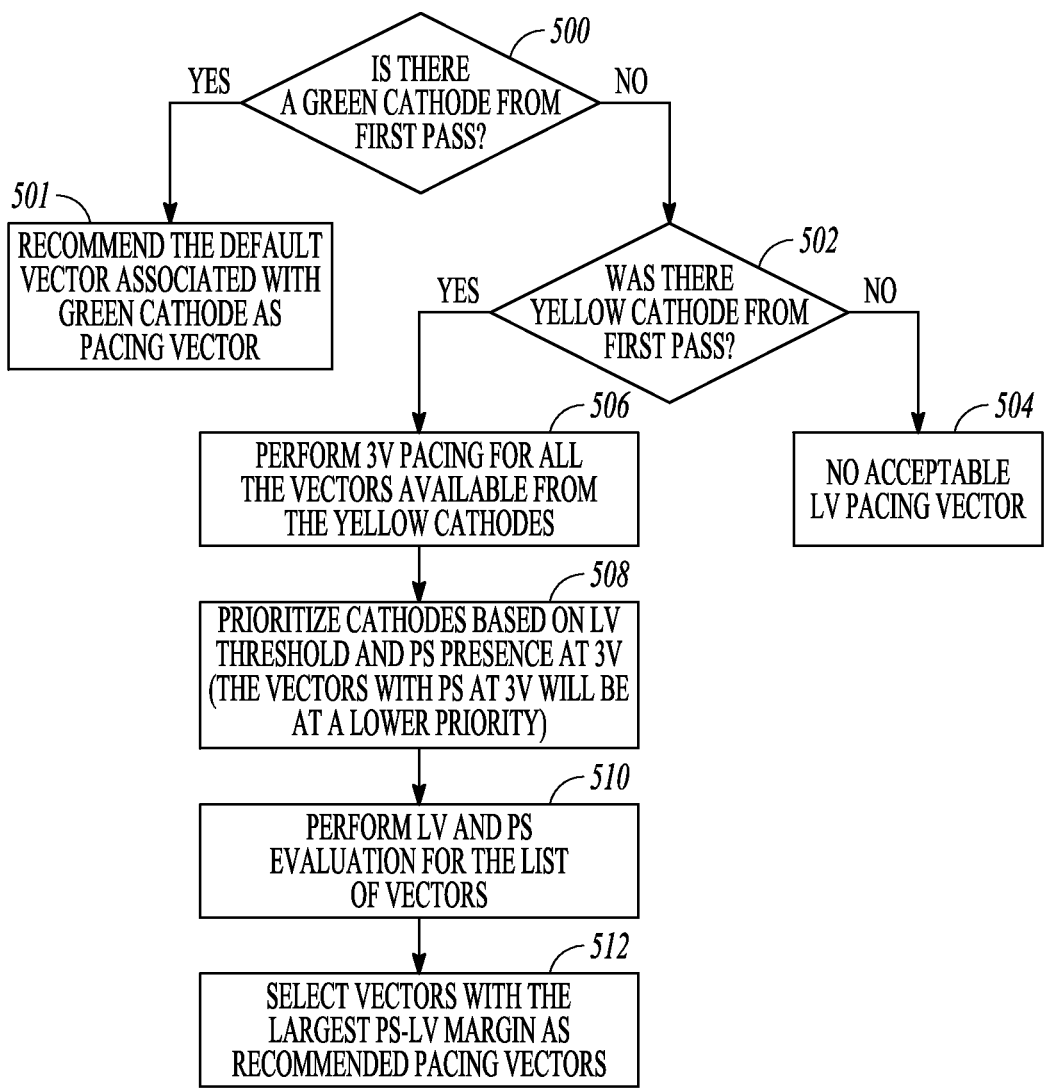
FIG. 5 is a flow diagram illustrating another portion of the example method for evaluating a plurality of vectors shown in FIG. 4.

FIG. 5 is a flow diagram illustrating another portion of the example method for evaluating a plurality of vectors shown in FIG. 4. In FIG. 5, a "second pass" is performed in which each electrode in the initially identified set of electrodes that was categorized as acceptable, e.g., cathodes categorized as green or yellow, is used as a cathode, and corresponding anodes can be evaluated to recommend pacing vectors. Or, if the first pass tested anodes, then cathodes are tested in the second pass.

One objective of the second pass of FIG. 5 is to recommend to a clinician, for example, one or more vectors with the lowest myocardial pacing threshold, e.g., left ventricle threshold or right ventricle threshold, and the largest phrenic stimulation margin.

In the first pass, described above with respect to FIG. 4, for a set of identified vectors, one (or more electrodes) was held constant as a predefined anode and the remaining electrodes of the set were cyclically tested as cathodes with the anode. Then, the cathodes were categorized.

Generally speaking, in the second pass of FIG. 5, for the set of identified vectors, if there are no green cathodes, each cathode that was identified in the first pass as being a possible candidate cathode that could be used for pacing, e.g., cathodes identified as yellow, is held constant as a cathode and the remaining electrodes of the set are cyclically tested as candidate anodes with each possible cathode. That is, the microprocessor 364 pairs one or more respective categorized acceptable first electrodes, e.g., cathodes, with one or more respective candidate second electrodes, e.g., anodes, capable of use therewith.

As described in more detail below with respect to FIG. 5, for each pairing, the microprocessor 364 delivers one or more second pacing stimuli at at least one second pacing energy. The microprocessor 364, determines whether, in response to the delivered second pacing stimulus, a cardiac depolarization occurred and whether a phrenic nerve stimulation occurred, the determination using physiological information received in response to the delivered at least one second pacing stimulus. The microprocessor 364 categorizes the pairings using information about at least one of whether cardiac depolarization occurred or whether phrenic nerve stimulation occurred. The microprocessor 364 evaluates the categorized pairings using information about a margin between the second pacing stimulus and the phrenic nerve stimulation threshold, and selects at least one pairing with the largest margin between the phrenic stimulation threshold and the myocardial pacing threshold, based on the evaluation, for use in subsequent ongoing delivery of pacing stimuli to the patient.

Referring now to FIG. 5, if the first pass of FIG. 4 identified a green cathode ("YES" branch of block 500), then the microprocessor 364 can recommend the vector, e.g., a default vector associated with the green cathode, to the user, e.g., via a display, and in some examples, stop the test (501). If, however, the first pass of FIG. 4 did not identify a green cathode ("NO" branch of block 500), then the microprocessor 364 can determine if there was a yellow cathode from the first pass (502). Again, the use of color to describe the acceptability of the electrode is only example implementation. Other example implementations can assign a number, letter, or some other status identifier to the cathodes to indicate their acceptability with respect to pacing efficacy.

If no yellow cathodes were identified in the first pass ("NO" branch of block 502), then the second pass is complete as no acceptable vectors were found for pacing (504). In such a case, it may be necessary to perform a more exhaustive search to find an acceptable pacing vector, which is beyond the scope of this disclosure but would be familiar to a person of ordinary skill in the art.

If a yellow cathode was found ("YES" branch of block 502), then the microprocessor 364 directs the device 101 to turn pacing on and the device 101 delivers at least one second pacing stimulus at at least one second pacing energy. The device 101 performs pacing at a set output level (506), e.g., left ventricle threshold test or right ventricle threshold test, at a pacing value near the middle of a set of pacing ranges, e.g., at about 3.0 V, for all the vectors available from the yellow cathodes. That is, one or more respective categorized acceptable first electrodes, e.g., cathodes, are paired with one or more respective candidate second electrodes, e.g., anodes, capable of use therewith.

Next, for each of the tested pairings of cathodes and anodes, the microprocessor 364 determines whether, in response to the delivered second pacing stimulus, a second cardiac depolarization occurred and whether a second phrenic nerve stimulation occurred, the determination using physiological information received in response to the delivered at least one second pacing stimulus. The microprocessor 364 categorizes the cathodes based on the myocardial pacing response, e.g., left ventricle capture or right ventricle capture, as well as the presence/absence of phrenic stimulation at 3 V (508). That is, the microprocessor 364 categorizes the pairings using information about at least one of whether the second cardiac depolarization occurred or whether the second phrenic nerve stimulation occurred.

In addition, in some example implementations, the categorized vectors can be prioritized. For example, the microprocessor 364 can prioritize the vectors that exhibit phrenic stimulation at 3 V lower than vectors that exhibit phrenic stimulation at higher voltages. If all of the vectors with a yellow cathode exhibit phrenic stimulation, then the microprocessor 364 can categorize the yellow cathodes and can prioritize the yellow cathode with the lowest myocardial pacing threshold as the most acceptable of the yellow cathodes (the highest priority of the yellow cathodes).

The acts associated with blocks 506 and 508 in FIG. 5 generally describe the blocks shown and described above with respect to FIG. 4. In other words, the techniques of the first pass of FIG. 4 are repeated as part of the second pass at blocks 506 and 508. For the purposes of conciseness, the first pass will not be described again.

After the pairings of electrodes, e.g., vectors, have been categorized and, in some examples, prioritized (508), the microprocessor 364 controls the device 101 to evaluate the individual myocardial pacing threshold and phrenic stimulation threshold for the categorized pairings (510). The evaluation of the categorized pairings, or set of vectors, is shown and described in more detail below with respect to FIG. 6. At this point, it is likely that the number of vectors in the categorized set of vectors is less than the initial set of vectors that were identified for testing prior to the first pass of FIG. 4.

After the evaluation of the individual myocardial pacing and phrenic stimulation thresholds, the microprocessor 364 can automatically, i.e., without requiring user intervention, select the vectors with the largest margin between the phrenic stimulation threshold and the myocardial pacing threshold as the recommended pacing vectors (512). That is, the microprocessor 364 can select at least one pairing, based on the evaluation, for use in subsequent ongoing delivery of pacing stimuli to the patient. In one example implementation, if the microprocessor 364 was unable to find any acceptable pacing vectors, then the pulse width of the pacing pulse can be modified, e.g., increased. In some examples, the pulse width of the pacing pulse can be increased in the first pass for one or more vectors if the first pass did not identify any green or yellow cathodes. Increasing the width of the pacing pulse can lower the pacing amplitude, and may help to avoid phrenic stimulation.

In some example implementations, anodal stimulation detection can be used for a coarser step threshold search to ensure that an identified threshold is real. Anodal stimulation detection is described in detail in U.S. Patent Application No.

2010/0262204 to McCabe et al., the entire content of which being incorporated herein by reference.

Figure 6:
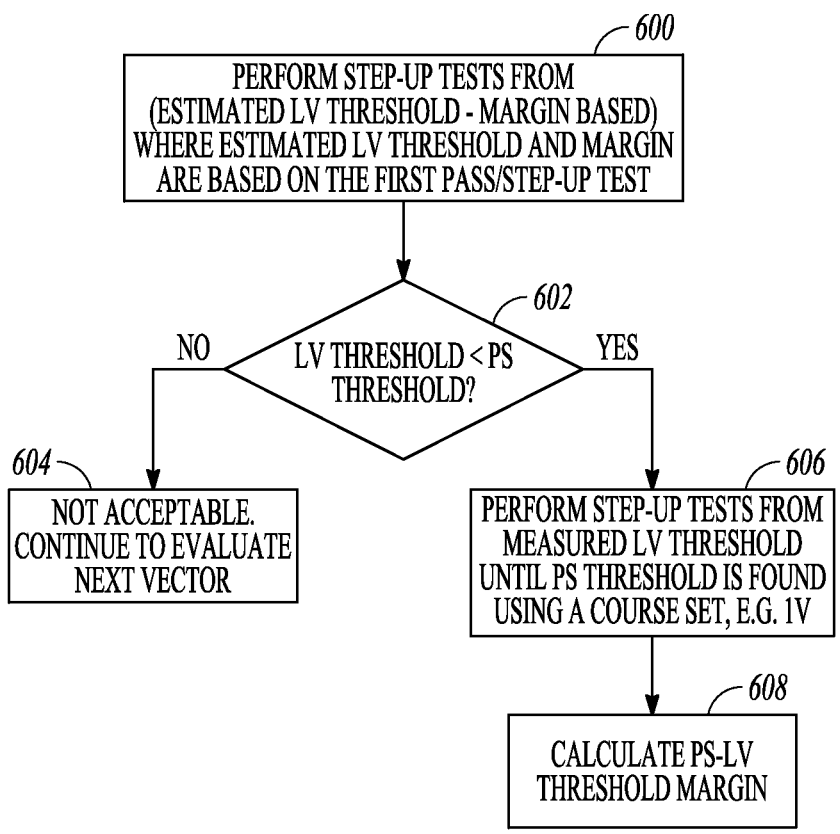
FIG. 6 is a flow diagram illustrating another portion of the example method for evaluating a plurality of vectors shown in FIGS. 4-5.

FIG. 6 is a flow diagram illustrating another portion of the example method for evaluating a plurality of vectors shown in FIGS. 4-5. More particularly, FIG. 6 depicts acts that microprocessor 364 can control device 101 to perform to evaluate the myocardial pacing and phrenic stimulation thresholds of individual vectors (following block 510 of FIG. 5). One objective of the evaluation shown in FIG. 6 is to find the vector with the best margin between phrenic stimulation and myocardial pacing thresholds.

At the top of FIG. 6, the microprocessor 364 can iteratively increase the amplitude of the pacing stimulus and device 101 can deliver another pacing stimulus, using the vector under evaluation. The increased amplitude value can begin at an estimated myocardial pacing threshold value minus a safety margin value (pacing threshold value—safety margin value), where the estimated myocardial pacing threshold value and the safety margin value are based on the step up test of the first pass of FIG. 4 (600). If the myocardial pacing threshold is not less than the phrenic stimulation threshold ("NO" branch of block 602), then the microprocessor 364 can determine that the vector is not acceptable and can begin to evaluate the next vector (604).

If the myocardial pacing threshold is less than the phrenic stimulation threshold ("YES" branch of block 602), then the microprocessor 364 can iteratively increase the amplitude of the pacing stimulus from the estimated myocardial pacing threshold and the device 101 can deliver another pacing stimulus, using the same vector initially selected, at the increased amplitude until phrenic stimulation occurs (606). In one example, the microprocessor 364 can iteratively increase, or step up, the amplitude of the pacing stimulus using step sizes that have fixed increments. As described above, in other examples, the step sizes can have variable increments, e.g., as determined by the pacing output voltage, or a binary search strategy can be used to iteratively increase the amplitude of the pacing stimulus until phrenic stimulation occurs.

After the microprocessor 364 performs the step-up tests, the microprocessor 364 can calculate the margin between the phrenic stimulation threshold and the myocardial pacing threshold (608). Then, as indicated above with respect to block 512 of FIG. 5, the microprocessor 364 can automatically select the vectors with the largest margin between the phrenic stimulation threshold and the myocardial pacing threshold, e.g., PS-LV margin, as the recommended pacing vectors.

In some example implementations, the list for potential vectors to perform the anode switching of FIG. 5 can be dynamic. That is, if there are multiple unacceptable or low PS-LV margins for vectors sharing the same cathode, then the microprocessor 364 can re-categorize the remaining vectors that share the same cathode. In one example, the microprocessor 364 can prioritize the remaining vectors that share the same cathode at a lower priority.

In one example implementation, an external device, e.g., clinician programmer, can place the device 101 and the external device in a special mode that allows quick lead measurements when the device 101 is used as pacing system analyzer (PSA) during the implant. In some examples, once in the special mode, the microprocessor 364 and the device 101 can perform the techniques described above.

In some example implementations, the techniques described above can be performed jointly by the device 101 and one or more devices external to the patient, e.g., a clinician programmer and/or PSA. That is, at least some of the functionality attributed to the microprocessor 364 of the device 101 can be performed by a microprocessor of the external device, e.g., external device 140 of FIG. 1, and the external device can use wired or wireless communication techniques to transmit instructions that, when executed, can control the device 101 to deliver the various pacing stimuli to the patient.

The techniques of this disclosure are not limited to a particular channel. Rather, the techniques can be applied to LV, RV, and atrial channels.

Figure 7:
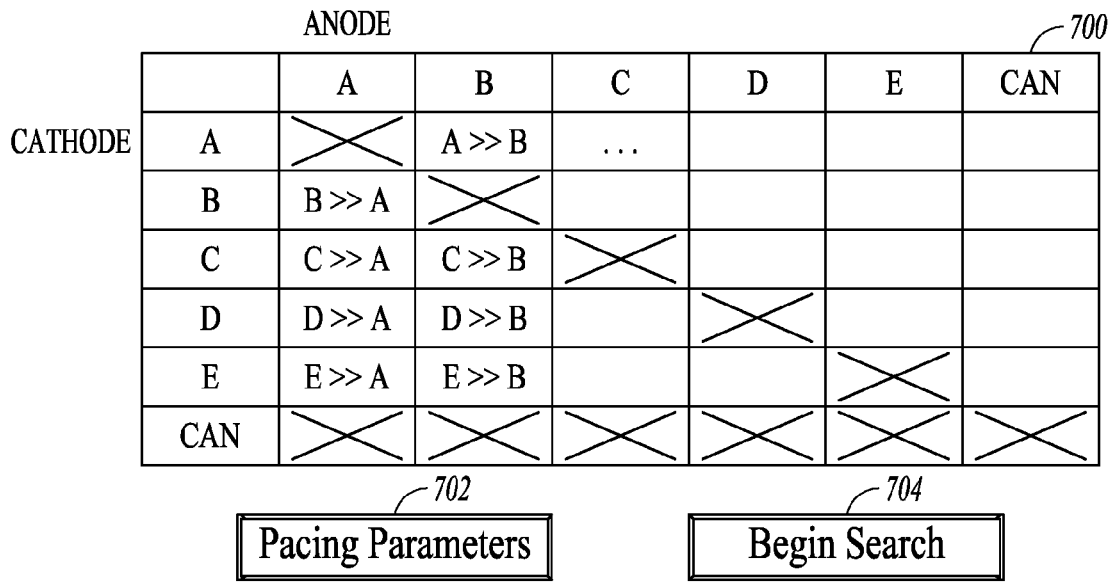
FIG. 7 is a schematic diagram illustrating an example user interface presented by an external device in accordance with this disclosure.

FIG. 7 is a schematic diagram illustrating an example user interface, e.g., user interface 145 of FIG. 1, presented by an external device in accordance with this disclosure. In FIG. 7 anode electrodes are displayed across the top of the grid and cathode electrodes are displayed along the left side. Within the grid 700, possible electrode pairings for testing are displayed. More particularly, possible electrode pairings for the first pass are displayed in which one or more electrodes are held constant as an anode and the remaining electrodes of the set are cyclically tested as cathodes with the anode. For example, the column under Anode "A," indicates that each of electrodes B-E are tested as cathodes with anode A, e.g., "B>>A," "C>>A," "D>>A," "E>>A." In the column under Anode "B," each of electrodes A, C-E are tested as cathodes with anode B, e.g., "A>>B," "C>>B," "D>>B," "E>>B." The remaining anode columns are similarly populated.

In the example grid 700 depicted in FIG. 7, the can is not used as a cathode. However, in some example configurations, it can be desirable to use the can as a cathode.

The user interface depicted in FIG. 7 can also include a "pacing parameters" icon 702 and a "begin search" icon 704. Selecting the "pacing parameters" icon 702 can allow a user, e.g., clinician, to manually enter pacing parameters or change existing pacing parameters, such as amplitude, pulse width, and the like. Selecting the "begin search" icon 704 can initiate the searching algorithm described in this disclosure and, in particular, with respect to FIGS. 4-6.

Figure 8:
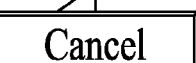
FIG. 8 is a schematic diagram illustrating another example user interface presented by an external device in accordance with this disclosure.

FIG. 8 is a schematic diagram illustrating another example user interface, e.g., user interface 145 of FIG. 1, presented by an external device in accordance with this disclosure. More particularly, FIG. 8 displays example evaluated categorized pairings via a user interface from a quick threshold search using the various techniques described above. In FIG. 8, the electrodes from which the device 101 is pacing are displayed along the left side of the grid, e.g., left ventricle tip electrode, left ventricle ring electrode, and the electrodes to which the device is pacing are displayed across the top, e.g., right ventricle electrode, can.

Within the grid 800, numerical values can be displayed for each threshold. For example, pacing from the LV tip to the LV ring, the test determined a 4.0 V phrenic stimulation threshold and a 1.0 V left ventricular threshold. In one example, the user interface can associate a color, e.g., yellow, with this electrode pairing to graphically illustrate the acceptability of this particular pacing vector.

As another example, pacing from the LV ring to the LV tip, the test determined a PS-LV margin of 1.0 V. In one example, the user interface can associate a color, e.g., yellow, with this electrode pairing to graphically illustrate the acceptability of this particular pacing vector.

In addition, the user interface of FIG. 8 can further include a "cancel" icon 802. A user can select the "cancel" icon 802 if a desirable, e.g., green, vector has been recommended and the user does not want to complete the test, or the microprocessor 364 can execute instructions that cause the test to automatically terminate once a desirable, e.g., green, vector has been found.

In some examples, the microprocessor 364 can automatically, i.e., without requiring user intervention, select electrode pairings, or vectors. In other examples, the microprocessor 364 can control a user interface to display the evaluated categorized pairings and a user, e.g., clinician, can select at least one pairing based on the evaluation via the user interface. In other words, the microprocessor 364 can receive, via the user interface, user input that selects at least one pairing, based on the evaluation.

Using the techniques of this disclosure, the time spent searching for thresholds, e.g., myocardial pacing thresholds and/or phrenic stimulation thresholds, can be greatly reduced. The techniques described above can quickly and efficiently shortlist possible pacing vectors and minimize phrenic nerve stimulation during threshold testing. By way of specific example, automatic detection of an LV threshold can be found for a heart rate of 60 beats-per-minute using the techniques of this disclosure in 10-15 seconds, while a regular threshold test can take about 2.5 minutes. For 10 vectors, the techniques of this disclosure can save about 20 minutes for each threshold testing.

In addition, at higher voltages in unipolar configurations, some patients feel discomfort or phrenic nerve/pocket stimulation. The techniques described in this disclosure, however, can avoid stimulating patients at higher voltages for unipolar configurations. Further, testing all possible vectors can be done less frequently. In addition, testing can be performed at a physician desired frequency.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects. Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code can be tangibly stored on one or more volatile or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A system comprising:
an implantable medical device configured to deliver pacing stimuli to a heart; and
at least one processor configured to:
for a set of at least two pacing vectors, wherein each vector is at least partially defined by a first electrode and a second electrode:
deliver at least one first pacing stimulus at a first specified pacing energy;
determine whether, in response to the delivered at least one first pacing stimulus, a first cardiac depolarization occurred and whether a first phrenic nerve stimulation occurred, the determination using physiological information received in response to the delivered at least one first pacing stimulus;
adjust the pacing stimulus to determine a first pacing threshold value; and
categorize acceptability of the first electrodes of the at least two pacing vectors using information about at least one of the determined first pacing threshold value, whether the first cardiac depolarization occurred, or whether the first phrenic nerve stimulation occurred;

pair one or more respective categorized acceptable first electrodes with one or more respective candidate second electrodes capable of use therewith, and for a particular pairing:
  deliver at least one second pacing stimulus at at least one second pacing energy;
  determine whether, in response to the delivered at least one second pacing stimulus, a second cardiac depolarization occurred and whether a second phrenic nerve stimulation occurred, the determination using physiological information received in response to the delivered at least one second pacing stimulus; and
  categorize the pairings using information about at least one of whether the second cardiac depolarization occurred or whether the second phrenic nerve stimulation occurred;
evaluate the categorized pairings using information about a margin between the second pacing stimulus and the second phrenic nerve stimulation threshold; and
select at least one pairing, based on the evaluation, for use in subsequent ongoing delivery of pacing stimuli.

2. The system of claim 1, wherein, prior to pairing one or more respective categorized acceptable first electrodes with one or more respective candidate second electrodes capable of use therewith, the at least one processor is configured to:
  recommend an electrode for pacing based on the categorized acceptability; and
  stop further evaluation of electrodes.

3. The system of claim 1, wherein the set of at least two pacing vectors comprises a set of default pacing vectors stored in a memory device, and wherein the set of at least two pacing vectors is less than the total number of pacing vectors available for pacing.

4. The system of claim 1, wherein the at least one processor is further configured to:
  rank or prioritize the categorized acceptable first electrodes.

5. The system of claim 1, wherein the first electrode includes a cathode and the second electrode includes an anode.

6. The system of claim 1, further comprising a user interface, wherein the at least one processor is further configured to:
  display, via the user interface, the evaluated categorized pairings, and
  wherein the at least one processor configured to select at least one pairing, based on the evaluation, is further configured to:
  receive, via the user interface, user input that selects at least one pairing, based on the evaluation.

7. The system of claim 1, further comprising a user interface, wherein the at least one processor configured to select at least one pairing, based on the evaluation, is further configured to:
  select, without requiring user intervention, at least one pairing, based on the evaluation.

8. The system of claim 1, wherein the implantable medical device comprises the at least one processor.

9. The system of claim 1, further comprising:
  a device external to a patient, wherein the external device comprises the at least one processor.

10. The system of claim 9, wherein the external device comprises at least one of a clinician programmer or a pacing system analyzer, and wherein the external device is configured to transmit information indicating the selected at least one pair of first and second electrodes to the implantable medical device.

11. A computer-readable medium comprising instructions that, upon execution, cause at least one processor to:
  for a set of at least two pacing vectors, wherein each vector is at least partially defined by a first electrode and a second electrode:
    deliver at least one first pacing stimulus at a first specified pacing energy;
    determine whether, in response to the delivered at least one first pacing stimulus, a first cardiac depolarization occurred and whether a first phrenic nerve stimulation occurred, the determination using physiological information received in response to the delivered at least one first pacing stimulus;
    adjust the pacing stimulus to determine a first pacing threshold value; and
    categorize acceptability of the first electrodes of the at least two pacing vectors using information about at least one of the determined first pacing threshold value, whether the first cardiac depolarization occurred, or whether the first phrenic nerve stimulation occurred;
  pair one or more respective categorized acceptable first electrodes with one or more respective candidate second electrodes capable of use therewith, and for a particular pairing:
    deliver at least one second pacing stimulus at at least one second pacing energy;
    determine whether, in response to the delivered at least one second pacing stimulus, a second cardiac depolarization occurred and whether a second phrenic nerve stimulation occurred, the determination using physiological information received in response to the delivered at least one second pacing stimulus; and
    categorize the pairings using information about at least one of whether the second cardiac depolarization occurred or whether the second phrenic nerve stimulation occurred;
  evaluate the categorized pairings using information about a margin between the second pacing stimulus and the second phrenic nerve stimulation threshold; and
  select at least one pairing, based on the evaluation, for use in subsequent ongoing delivery of pacing stimuli.

12. The computer-readable medium of claim 11, wherein, prior to pairing one or more respective categorized acceptable first electrodes with one or more respective candidate second electrodes capable of use therewith, the at least one processor is configured to:
  recommend an electrode for pacing based on the categorized acceptability; and
  stop further evaluation of electrodes.

13. The computer-readable medium of claim 11, wherein the set of at least two pacing vectors comprises a set of default pacing vectors stored in a memory device, and wherein the set of at least two pacing vectors is less than the total number of pacing vectors available for pacing.

14. The computer-readable medium of claim 11, wherein the at least one processor is further configured to:
  rank or prioritize the categorized acceptable first electrodes.

15. A method of determining at least one cardiac pacing vector, the method comprising:
  for a set of at least two pacing vectors, wherein each vector is at least partially defined by a first electrode and a second electrode:
    delivering at least one first pacing stimulus at a first specified pacing energy;

determining whether, in response to the delivering the at least one first pacing stimulus, a first cardiac depolarization occurred and whether a first phrenic nerve stimulation occurred, the determining using physiological information received in response to the delivering the at least one first pacing stimulus; and adjusting the pacing stimulus to determine a first pacing threshold value;

categorizing acceptability of the first electrodes of the at least two pacing vectors using information about at least one of the determined first pacing threshold value, whether the first cardiac depolarization occurred, or whether the first phrenic nerve stimulation occurred;

pairing one or more respective categorized acceptable first electrodes with one or more respective candidate second electrode capable of use therewith, and for a particular pairing:

delivering at least one second pacing stimulus at at least one second pacing energy;

determining whether, in response to the delivering the at least one second pacing stimulus, a second cardiac depolarization occurred and whether a second phrenic nerve stimulation occurred, the determining using physiological information received in response to the delivering the at least one second pacing stimulus; and categorizing the pairings using information about at least one of whether the second cardiac depolarization occurred or whether the second phrenic nerve stimulation occurred;

evaluating the categorized pairings using information about a margin between the second pacing stimulus and the second phrenic nerve stimulation threshold; and selecting at least one pairing, based on the evaluation, for use in subsequent ongoing delivery of pacing stimuli.

16. The method of claim 15, further comprising:

prior to pairing one or more respective categorized acceptable first electrodes with one or more respective candidate second electrodes capable of use therewith:

recommending an electrode for pacing based on the categorized acceptability; and stopping further evaluation of electrodes.

17. The method of claim 15, wherein the set of at least two pacing vectors comprises a set of default pacing vectors stored in a memory device, and wherein the set of at least two pacing vectors is less than the total number of pacing vectors available for pacing.

18. The method of claim 15, further comprising ranking or prioritizing the categorized acceptable first electrodes.

19. The method of claim 15, wherein the first electrode includes a cathode and the second electrode includes an anode.

20. The method of claim 15, further comprising:

selecting, without requiring user intervention, at least one pairing, based on the evaluation.

* * * * *